(12) United States Patent
Morad et al.

(10) Patent No.: US 11,141,328 B1
(45) Date of Patent: Oct. 12, 2021

(54) HIGH CAPACITY HYGIENE PRODUCT DISPENSER

(71) Applicant: THE TRANZONIC COMPANIES, Cleveland, OH (US)

(72) Inventors: Fred I. Morad, Toluca Lake, CA (US); Robert A. Acosta, Norwalk, CA (US)

(73) Assignee: THE TRANZONIC COMPANIES, Cleveland, OH (US)

( * ) Notice: Subject to any disclaimer, the term of this patent is extended or adjusted under 35 U.S.C. 154(b) by 0 days.

(21) Appl. No.: 17/220,458

(22) Filed: Apr. 1, 2021

(51) Int. Cl.
| G07F 11/16 | (2006.01) |
| A61F 15/00 | (2006.01) |
| B65D 83/02 | (2006.01) |
| A47F 1/10 | (2006.01) |
| G07F 11/04 | (2006.01) |

(52) U.S. Cl.
CPC .............. *A61F 15/003* (2013.01); *A47F 1/10* (2013.01); *A61F 15/001* (2013.01); *B65D 83/02* (2013.01); *G07F 11/04* (2013.01); *G07F 11/16* (2013.01)

(58) Field of Classification Search
CPC ................................ A61F 15/003; A47F 1/10
See application file for complete search history.

(56) References Cited

U.S. PATENT DOCUMENTS

| 5,579,952 A | * | 12/1996 | Fiedler | G07F 9/105 219/521 |
| 2015/0289731 A1 | * | 10/2015 | Lee | A47K 10/426 221/45 |
| 2018/0025572 A1 | * | 1/2018 | Morad | G07F 9/04 221/6 |

* cited by examiner

*Primary Examiner* — Gene O Crawford
*Assistant Examiner* — Ayodeji T Ojofeitimi
(74) *Attorney, Agent, or Firm* — Taft Stettinius & Hollister LLP; Ryan O. White; Daniel J. Krieger (57) ABSTRACT

A dispensing apparatus of hygiene products including dispensing of feminine pads and tampons activated by non-contact sensor. The dispensing apparatus including a back portion, a side portion coupled to the back portion, and a housing door movably coupled to the side portion. A module is rotatably coupled to the housing and includes a tray and at least one tray door assembly operatively coupled to the tray. The tray door assembly defines an interior space with the tray, wherein the interior space stores the hygiene products to be dispensed.

20 Claims, 10 Drawing Sheets

HIGH CAPACITY HYGIENE PRODUCT DISPENSER

FIELD OF THE DISCLOSURE

The present disclosure relates to vending machines that dispense hygiene products. More specifically, the present disclosure relates to vending machines that dispense feminine hygiene products in response to an activation of a sensor without requiring the depositing of coins or requiring payment of any other compensation.

BACKGROUND OF THE DISCLOSURE

Different types of vending machines dispense hygiene products in response to a buyer depositing money at the machine either in hard currency, such as coinage or paper bills. Other types of vending machines dispense hygiene products in response to activation of a contact or non-contact sensor without the need to deposit any type of money. Such machines are often located in the restrooms of public or corporate buildings to dispense feminine hygiene products. The owners or proprietors of such facilities provide the feminine hygiene products without remuneration, since such products are considered to be essential and as such are provided free of charge. Since these hygiene product dispensers are often located in high traffic areas, the dispensing machine can run out of product fairly often and requires refilling on a regular basis throughout the day. Product dispensers of this type require that products are loaded into the dispenser one product at a time, which takes a lot of time. Consequently, the frequency of refilling the product dispenser is often greater than the amount of time available to refill the product dispenser. What is needed therefore, is a hygiene product dispenser having a high capacity that can be rapidly filled to prevent individuals from being dissatisfied when a dispenser is empty.

SUMMARY

The present invention, in one embodiment, includes a vending machine which contains rows of feminine hygiene products adjacent one another, with sanitary pads in one row and tampons in a second row. Other types of hygiene products and vending machines therefore are contemplated, such as hygiene products for men. The products are aligned in columns, one above the other within the row. There is an aligned horizontal dispensing platform on which the lowest feminine hygiene product is retained which assists in dispensing the retained lowermost feminine hygiene product and assists in receiving the next lowermost feminine hygiene product. For a machine having two or more columns of different types of products, there is one or more aligned horizontal dispensing platforms on which the lowest feminine hygiene product is retained which assists in dispensing the retained lowermost feminine hygiene product and assist in receiving the next lowermost feminine hygiene product. Other embodiments are contemplated and include a dispenser that dispense one or more rows arranged in columns of the same type of product or of different types of products.

The operation of the vending machine is controlled by a computer chip affixed to a motherboard. Actuation of non-contact sensors affixed to a module located in the product dispensing machine dispense a selected product. A power pack, which in one embodiment, is a battery pack having four (4) C-sized batteries, is connected to one or more connectors to the motherboard. A door switch is also connected to connectors on the motherboard to indicate that the door is closed or opened.

Dispensing of products is controlled by the computer chip at the motherboard. Built into the computer is a time delay so that someone cannot empty the machine by continuously touching the sensor for dispensing either feminine napkins or tampons. Once a product such as a feminine napkin is dispensed, the computer program causes a time delay of about 5 seconds. In other embodiments, other time delays are contemplated including time delays of anywhere from two seconds to ten seconds, or more, before either another feminine napkin or a tampon is dispensed. Therefore, the time delay causes an ability to immediately inactivate the machine to dispense a second product and the time delay prevents someone from continuously activating the sensor to dispense all of the products in the machine. The time delay works both ways for all products. If a tampon is dispensed, then the time delay prevents a second tampon or a first feminine napkin from being dispensed until the computer set time such as two seconds to thirty seconds has elapsed.

In one embodiment, there is one electronic assembly for each product. There is one circuit board and one set of connectors with connecting wires for the sanitary pads. There is a second separate circuit board and second set of connectors with connecting wires for the tampons.

It is also within the spirit and scope of the present disclosure to have one circuit board (also called the motherboard) as disclosed herein which is hardwired to separate sensors for dispensing products stored in the apparatus.

The present apparatus includes a housing of a plastic or other comparable container with a cover made of different materials and preferably opaque. In one embodiment, there is provided a vending machine with a cover which conceals the circuit boards and sensors on the back of the cover for both the dispensing of sanitary pads, tampons, and other products that facilitates the transmission of signals through a printed circuit board to carry out the signals as described above to cause the activation by hand signal.

In different embodiments, a dispenser dispenses feminine hygiene products including sanitary napkins and tampons by a simple hand motion without requiring any direct physical contact on the part of the person such as placing coins in the machine or rotating a handle or performing any other comparable physical activity. While such activities may be simple for younger and healthier people, as the population ages, it is more difficult for older people to do the simplest tasks such as rotating a heavy handle or placing the right amount of coins inside a machine. Therefore, by not having to do anything other than actuating the appropriate sensor by a wave of the hand or other object, the difficulty in obtaining a sanitary pad or tampon is substantially reduced.

In one embodiment, there is provided a dispensing apparatus for dispensing hygiene products. The apparatus includes a housing having a back portion, a side portion coupled to the back portion, and a housing door movably coupled to the side portion. A module is rotatably coupled to the housing, wherein the module includes a tray and at least one tray door assembly operatively coupled to the tray. The tray door assembly defines an interior space with the tray, wherein the interior space stores hygiene products to be dispensed.

In another embodiment, there is provided a dispensing apparatus for dispensing hygiene products. The apparatus includes a housing having a back portion, a side portion coupled to the back portion, and a housing door movably coupled to the side portion. A module is rotatably coupled to the housing, wherein the module includes: i) a tray defining an interior space to temporarily store hygiene products; ii) a divider located in the space to divide the space into a first portion and a second portion; iii) a first tray door rotatably coupled to the tray to limit access to the first portion when the first tray door is closed; and iv) a second tray door rotatably coupled to the tray to limit access to the second portion when the second tray door is closed. The module further includes a bottom portion located adjacent to the tray and a dispensing device located at the bottom portion, wherein the dispensing device dispenses the first hygiene product and the second hygiene product.

In a further embodiment, there is provided a method of dispensing hygiene products including the steps of: enabling the rotation of a hygiene product module away from a housing to expose a module door; releasing the door from the module to expose a space in the module; supporting hygiene products in the space; temporarily storing the supported hygiene products in the space upon latching of the door to the module; dispensing the stored hygiene products from the space; deflecting the dispensed stored hygiene products away from module electronics towards a dispensing shelf; and illuminating a light upon the dispensing of one of the stored hygiene products.

Further novel features and other aspects of the present invention will become apparent from the following detailed description and discussion.

BRIEF DESCRIPTION OF THE DRAWINGS

Referring particularly to the drawings for the purpose of illustration only and not limitation, there is illustrated.

DETAILED DESCRIPTION OF THE EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention.

Figure 1:
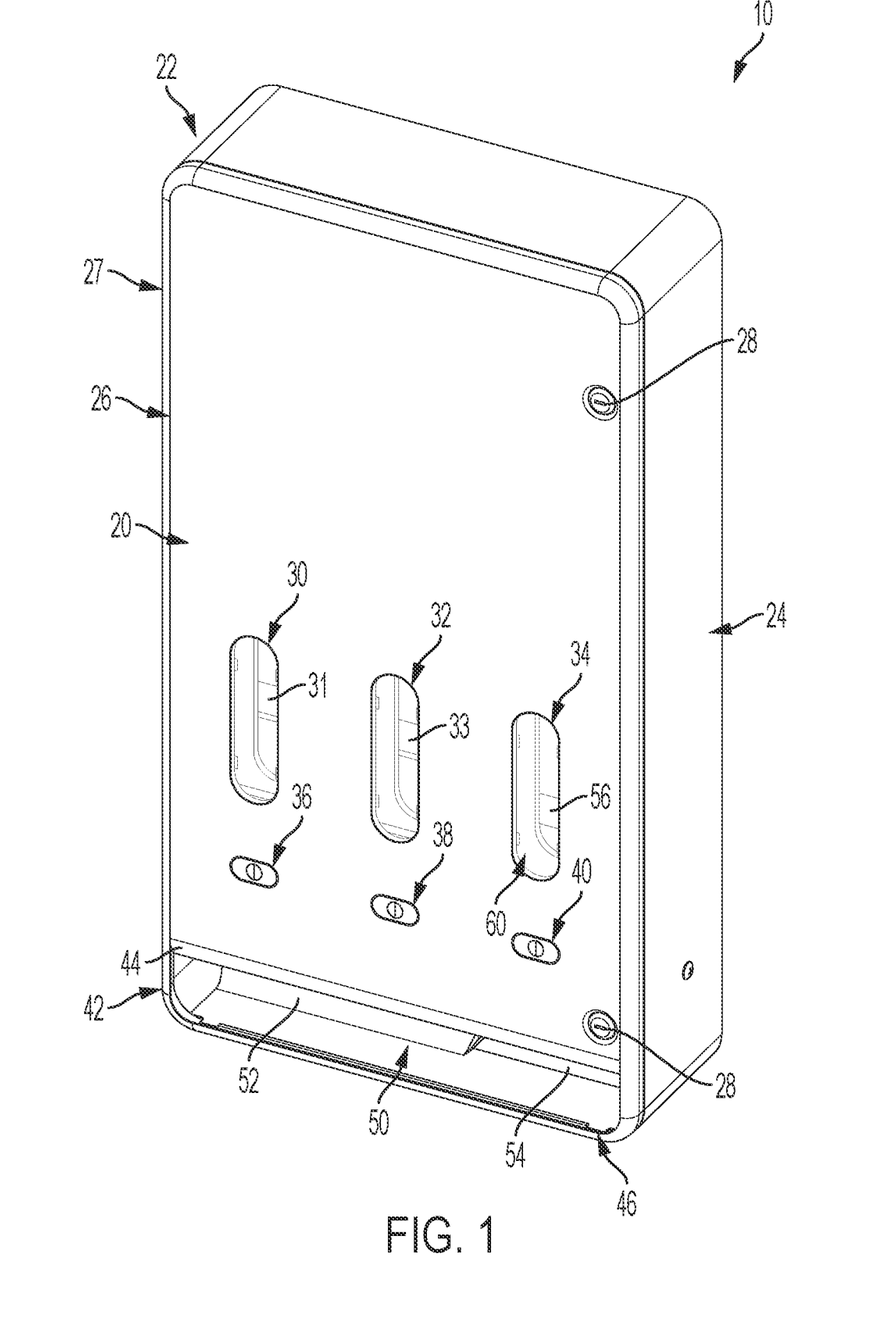
FIG. 1 illustrates an elevational perspective front view of a dispenser apparatus in a closed condition.

FIG. 1 illustrates a feminine hygiene product dispensing apparatus 10. The apparatus 10 includes a front door 20 coupled to a cabinet or housing 22 having a side portion 24 coupled to a back wall 25 (see FIG. 3). The front door 20 is hinged to a side portion 27 with a hinge 26 to enable the door 20 to open when locks 28 are unlocked. In other embodiments, one or more locks 28 are included and can be located on the side portion 24 or other locations.

The door 20 includes a first window 30, a second window 32, and a third window 34. Each of the windows 30, 32, and 34 includes a transparent lens each of which is sufficiently transparent to view hygiene products located within the apparatus 10. Accurate selection of hygiene products is determined by viewing the product being selected through the appropriate window. When there is no product that can be seen, there are no more products available in that stack of products. Beneath each of the windows is located a sensor lens, including a first sensor lens 36, a second senor lens 38, and a third sensor lens 40. Located behind each of the sensor lenses is a sensor configured to dispense a product from a stack or vertically oriented row of products which can be seen through a corresponding window. For instance, activation of a sensor behind lens 30 dispenses a product 31 from the stack of products seen through the first window 30. Likewise, activation of a sensor behind lens 38 dispenses a product 33 from the stack of products seen through the second window 32. Each of the stacks of products are stored in a module 60, the details of which are described later herein.

Once one of the products is dispensed, the product falls into product receiving area 42, which is defined between a bottom portion 44 of the door 20 and a base 46 defined by the side portion 24. A product ramp 50 includes a first ramp 52 and a second ramp 54 each of which is configured to direct a product dispensed from one of the stacks of products to the base 46. In one embodiment, the first ramp 52 includes a curved surface that extends across the width of a first product 31 stored behind the window 30 and a second product 33 stored behind the window 32. In this case, the first product and the second product are of the same type and the first ramp 52 extends across a length both products. A second ramp 54 receives a product 56 located in a stack of products seen at the third window 34. In this embodiment, the products 56 are of a different configuration than either of the products 31 or 33 and the second ramp 54 is sized and shaped differently than the first ramp 52. When the products 56 are tampons, for instance, the shape of tampon is generally cylindrical and tends to roll when dispensed. To substantially prevent the dispensed tampon from rolling off of the base 46 and out of the dispenser 10, the ramp 54 is recessed further within the access area 42 when compared to the first ramp 52. This recess helps insure that the tampon, if it should roll along the surface, stops rolling on the surface of base 46 before is rolls can roll out of the access area 42.

Figure 2:
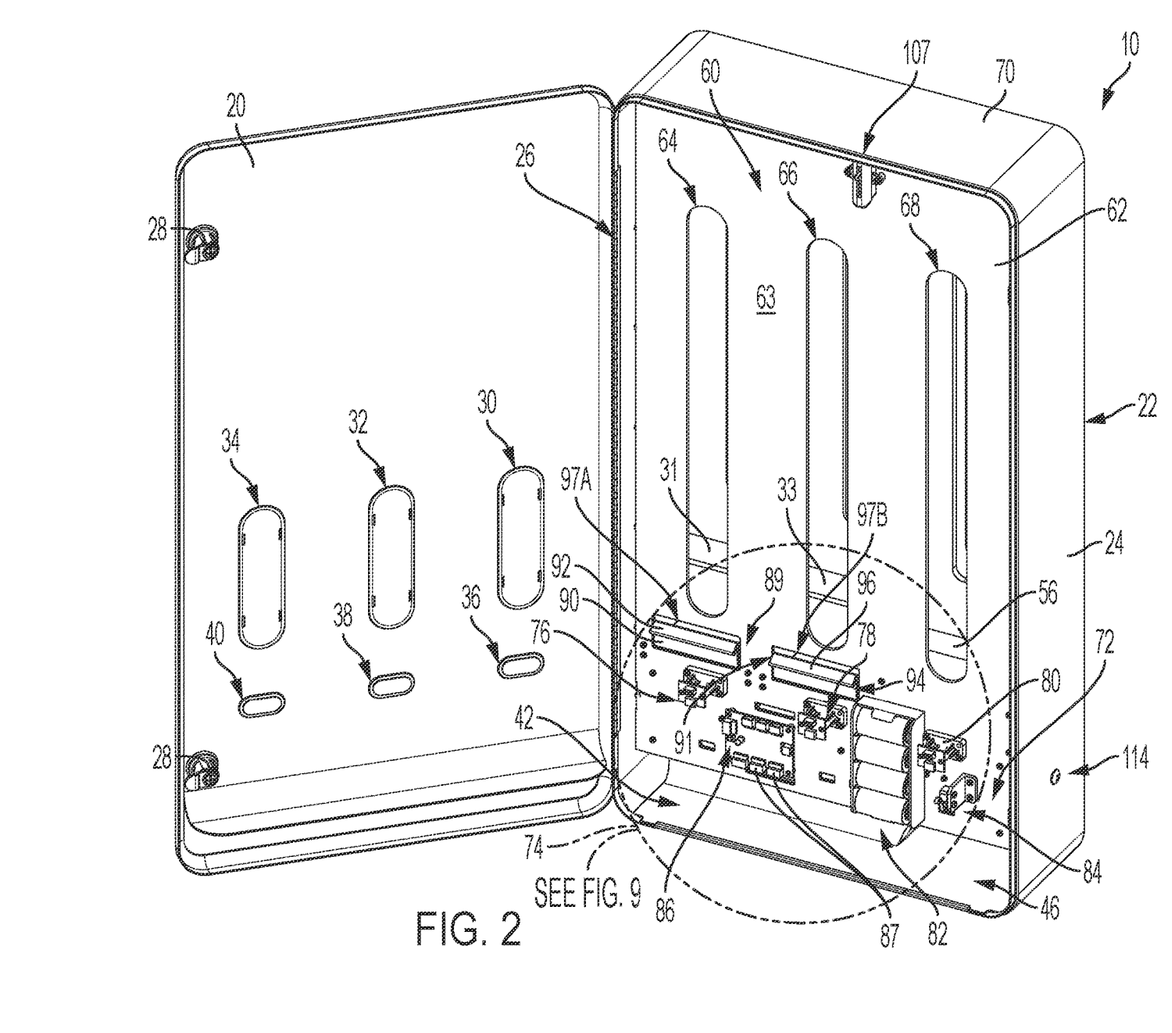
FIG. 2 illustrates an elevational perspective front view of a dispenser apparatus in an open condition.

FIG. 2 illustrates an elevational perspective front view of the dispensing apparatus 10 with the door 20 in an open condition. The product module 60 is located within a space defined by the door 20, the side portion 24, and the back wall 25 of the housing 22. The product module 60 includes a front wall 62 that includes a first portion 63 defining a first elongated aperture 64, a second elongated aperture 66, and a third elongated aperture 68. Each of these apertures is configured to enable viewing of respective products 31, 33, and 56 though the apertures and though respective windows 30, 32, and 34 when the door 20 is closed. The front wall 62 extends from a top wall 70 of the housing 22 to the access area 42 and as such defines the access area 42 with the base 46. A second portion 72 of the front wall 62, below the elongated apertures, provides support for a dispensing apparatus 74.

Figure 6:
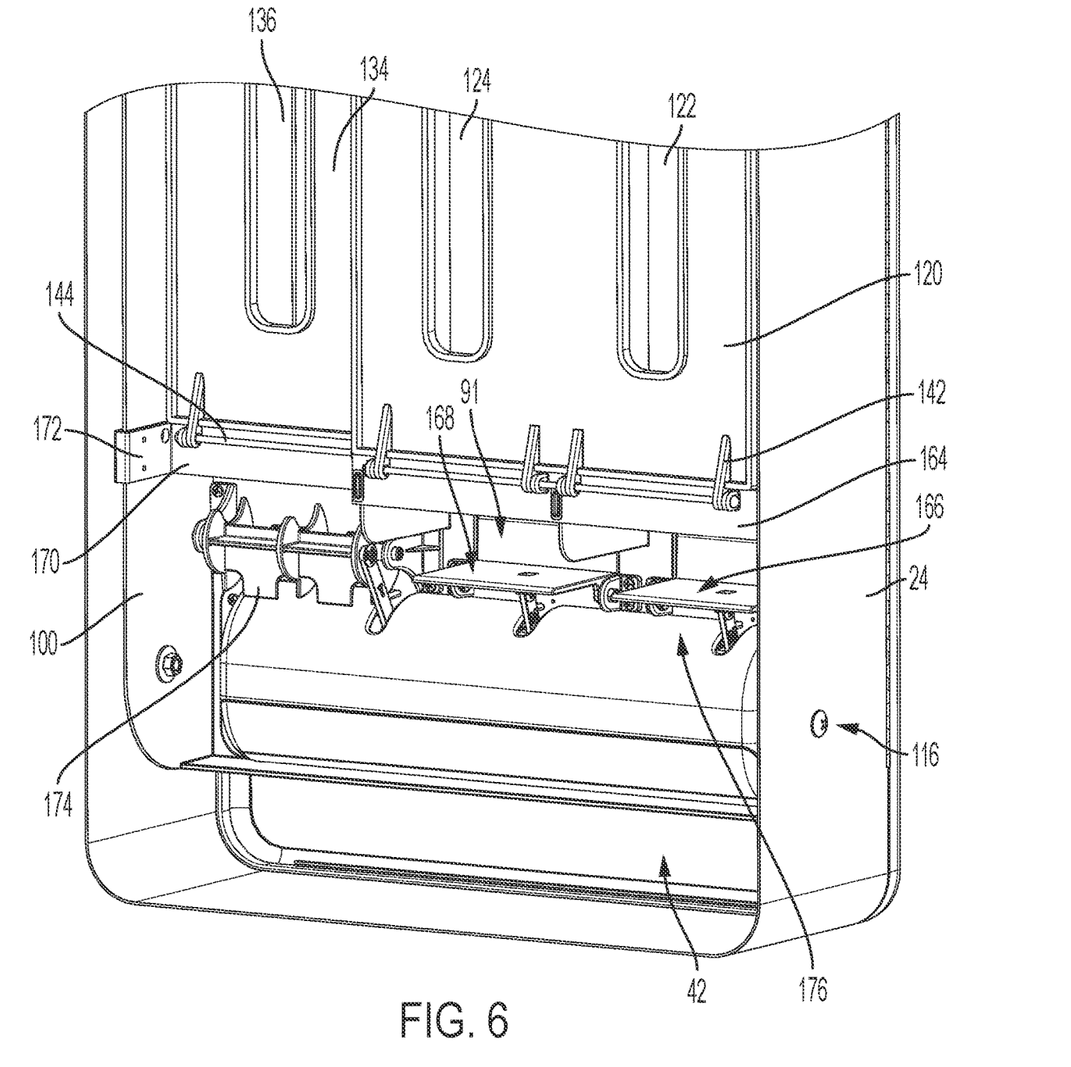
FIG. 6 illustrates an elevational perspective back view of a bottom portion of a dispenser apparatus with a product ramp removed.
Figure 7:
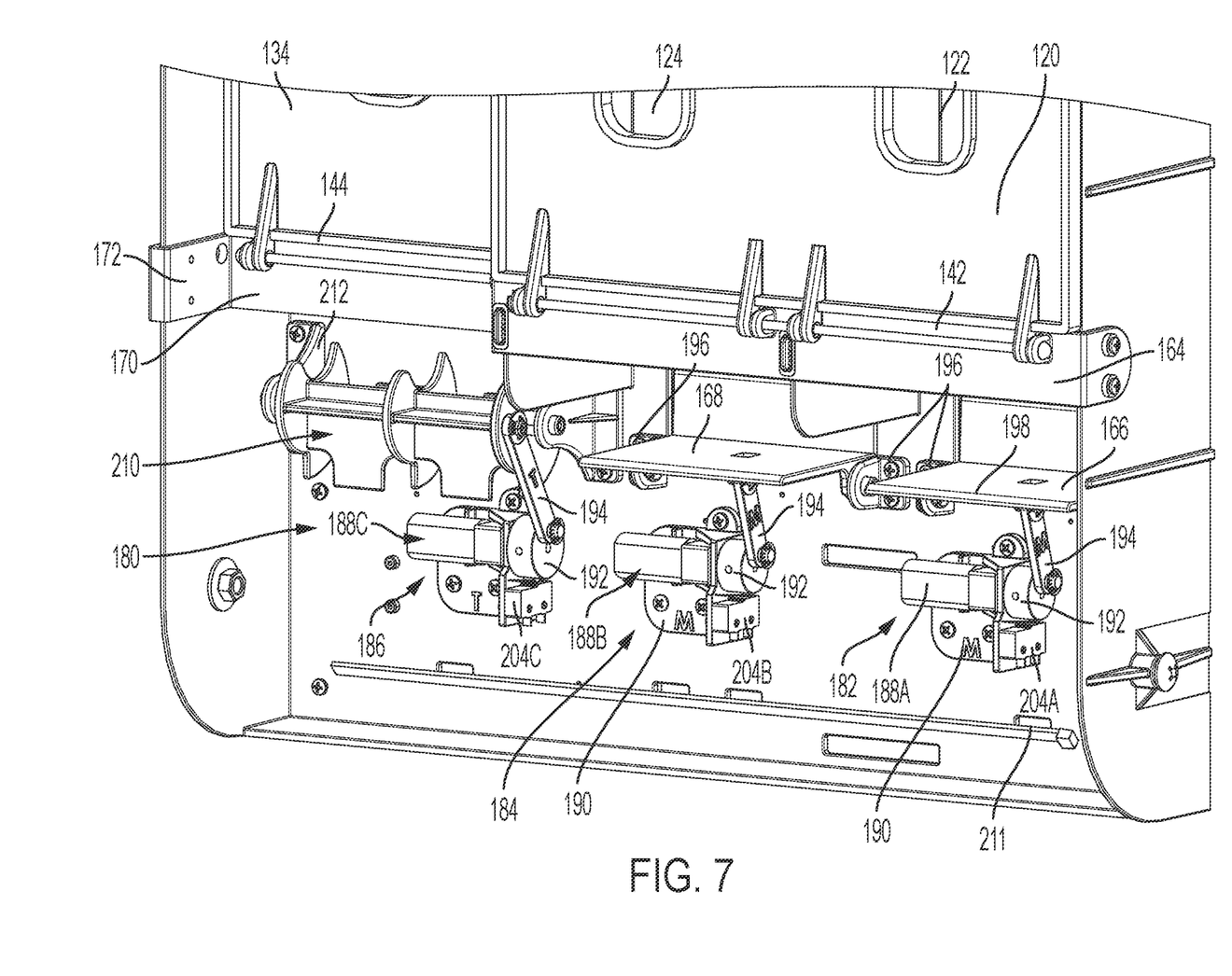
FIG. 7 illustrates an elevational perspective back view of a bottom portion of a dispenser apparatus with a product deflector removed.
Figure 8:
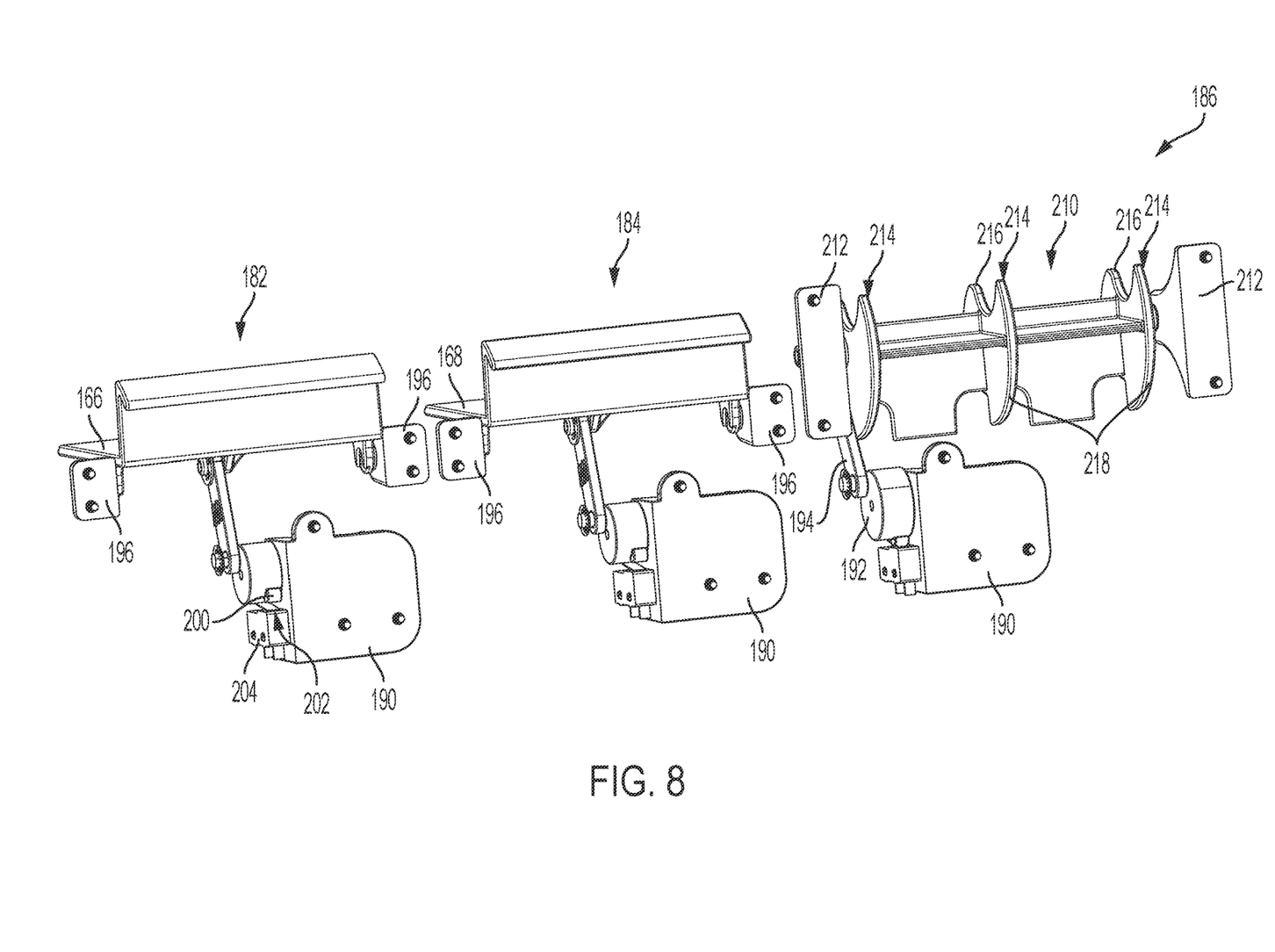
FIG. 8 illustrates dispensing mechanisms of a dispenser apparatus.
Figure 9:
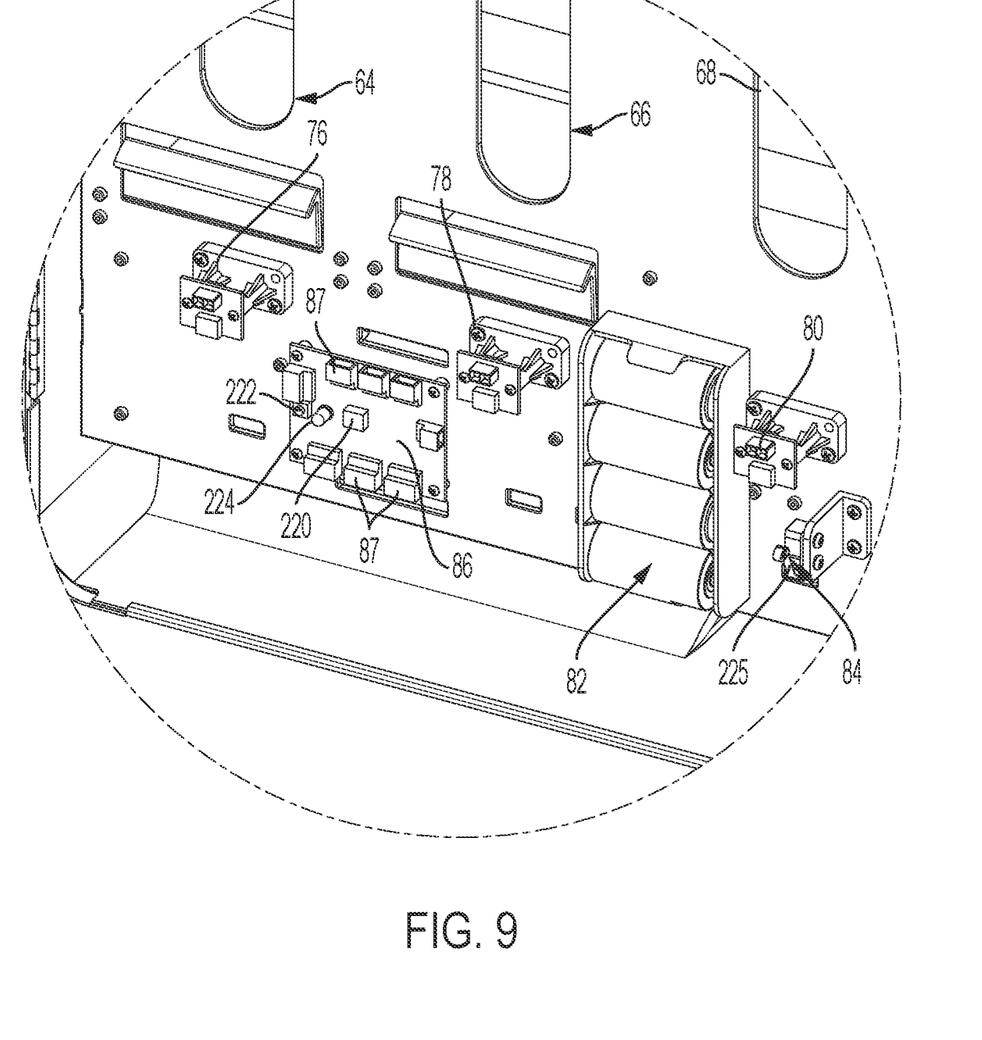
FIG. 9 illustrates an elevational perspective front view a bottom portion of a dispenser apparatus in an open condition showing a dispenser device.

The dispensing apparatus 74 includes a plurality of devices located on either side of the front wall 62 as illustrated in FIGS. 2, 7, and 9. In FIG. 2, the devices include a first motion sensor 76, a second motion sensor 78, a third motion sensor 80, a power supply 82, and door switch 84, each of which is electrically connected to a motherboard 86. The motherboard 86 supports connectors 87 for receiving and transmitting electrical signals to and from the various devices. In one embodiment, the power supply 82 includes a housing to receive disposable or rechargeable batteries, such as C sized batteries. In another embodiment, the power supply 82 includes a power converter connected to a power cord for connecting to a source of AC power. A first product receiver 89 includes a door 90 having a door flap 92 and a second product receiver 91 includes a door 94 having a door flap 96. The product receivers include dispenser platforms 166 and 168 as seen in FIGS. 6, 7, and 8. A space, or slit, 97A and a space 97B is located above the door flap 96 to provide clearance for rotation of the product receivers 89 and 91.

Figure 3:
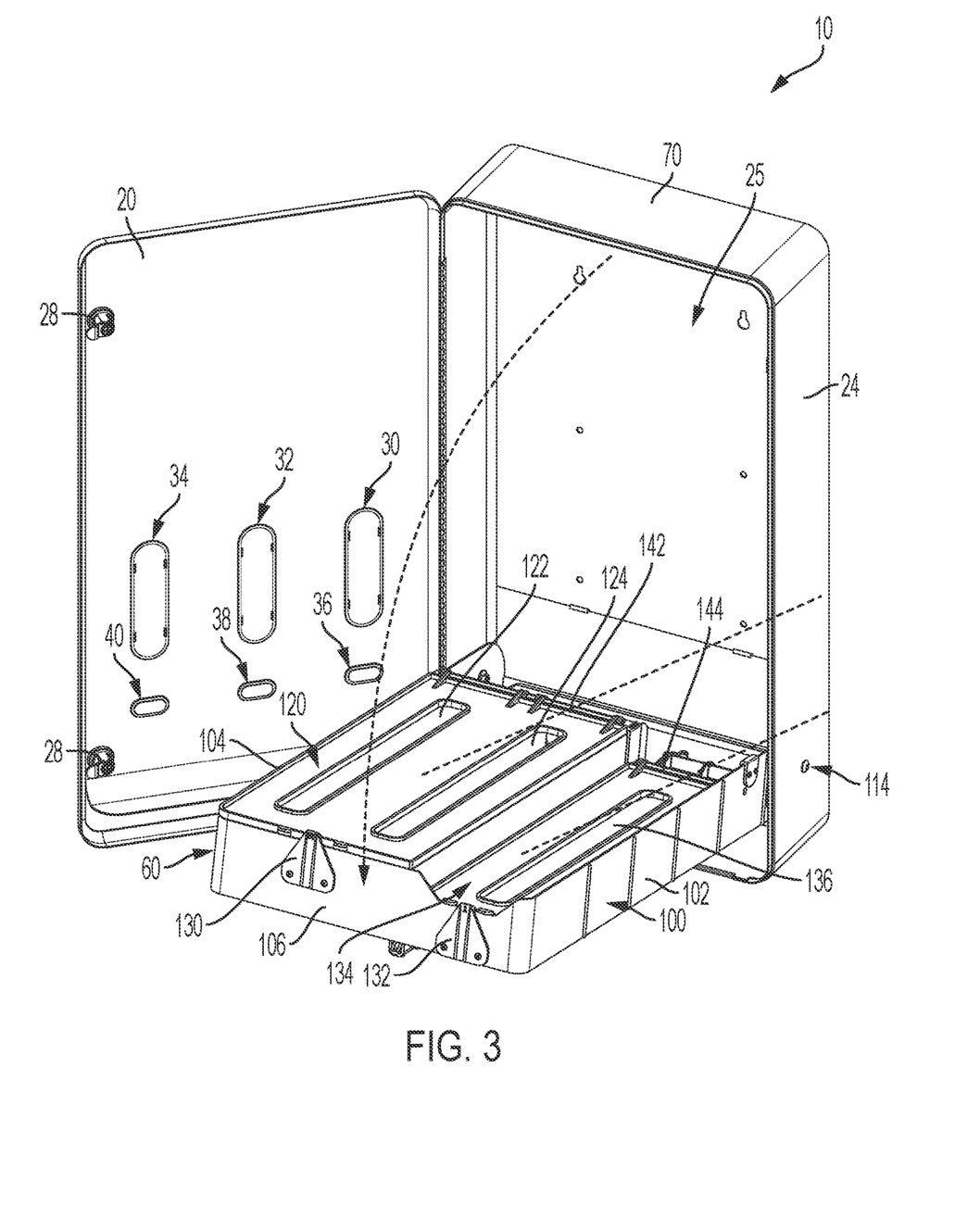
FIG. 3 illustrates an elevational perspective front view of a dispenser apparatus in an open condition with a dispenser module in a lowered position and closed condition.
Figure 4:
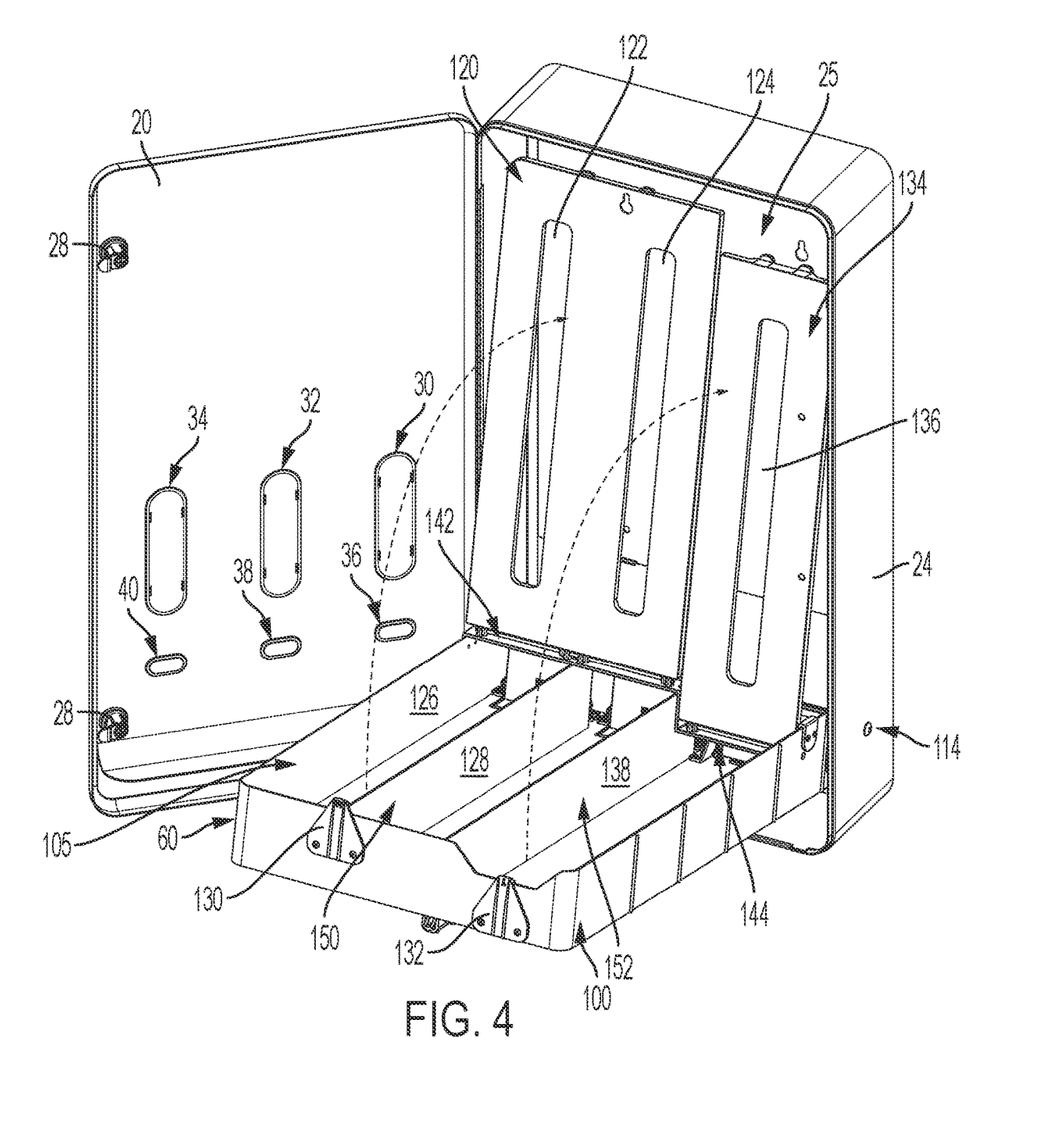
FIG. 4 illustrates an elevational perspective front view of a dispenser apparatus in an open condition with a product module in a lowered position and an opened condition.

FIGS. 3 and 4 illustrate elevational perspective front views of the dispenser apparatus 10 with the door 20 in an open condition and product module 60 in a lowered position which holds and stores hygiene products. When the product module 60 is in the lowered position, the products being stored can be bulk loaded, which eliminates the need to load products one at a time. By bulk loading two or more products at a time into the product module, loading time is significantly reduced which increases the amount of time available for an individual to complete other tasks.

The product module 60 includes a product holding tray 100 which includes the front wall 62 shown in FIG. 2 and further includes a first side wall 102, a second side wall 104, and a top wall 106, which define an interior space 105 that extends from the first side wall 102 to the second side wall 104, as illustrated in FIG. 4. A module release trigger 107 of FIG. 2 holds the module 60 in the raised position and when released enables movement of the module 60 to the lowered, or loading, position of FIG. 3.

The module 60 includes a first product door 120 having first and second viewing slots 122 and 124 that enable an inspection of first and second product storage areas 126 and 128, which are part of the interior space 105, as seen in FIG. 4. A first door catch 130 is connected to the top wall 106 to maintain the first product door 120 illustrated in a closed condition in FIG. 3. The module 60 further includes a second product door 134 including a viewing slot 136 that enables inspection of a third product storage area 138 of FIG. 4. A second door catch 132 is connected to the top wall 106 to hold the second product door 134 in a closed position as illustrated in FIG. 3. Both the first product door 120 and the second product door 134 rotate respectively about a first hinge 142 and a second hinge 144. The first and second door catches 130 and 132 are resilient and extending tabs that are pushed to release the doors.

As seen in FIG. 4 when the module 60 is in the lowered position, the first door 120 when opened, in the direction of the arrow, exposes both of the interior storage areas 126 and 128. A product divider 150 is located in a portion of the tray to define each of the interior storage areas 126 and 128. In this embodiment, a product of a single type, both products 31 and 33, is loaded in each of the storage areas 126 and 128 such that a product from storage area 126 is dispensed upon activation of motion sensor 76 and a product from storage area 128 is dispensed upon activation of motion sensor 78. A product of a different type, such as product 56, is loaded in storage area 138, upon opening of the door 134 in the direction of the arrow.

In the illustrated embodiment of FIG. 4, the divider 150 is located to set the storage areas 126 and 128 to have equal widths to accommodate two stacks of products of the same type, or two products of different types having the same or similar size. In this embodiment, the divider is fixed. In other embodiments, if the divider 150 is located to define storage areas of different sizes, products of two different types are stored in interior storage areas 126 and 128. In a further embodiment, the divider 150 is adjustable and movable laterally from side to side to change the size of the interior storage areas 126 and 128.

A divider 152 is located between the storage area 128 and the storage area 138 which defines a space sized to accommodate products of a different type or of a different size than those stored in areas 126 and 128. In different embodiments, the divider 152 is either fixed or is adjustably movable. In one or more embodiments, each of the storage areas is of the same width or of different widths, or two of the storage areas are the same width the remaining storage area of a different width. In still other embodiment, products of different sizes are dispensed with fixed dividers 150 and 152. In these embodiment, an insert is place next to one or both of the dividers to provide storage areas having widths selected for different sized products. The insert reduces a width of the area to accommodate different sized products.

When the doors 120 and 134 are opened, products are placed for storage in and later dispensed from areas 126, 128, and 138. The products are stacked side by side in each storage area, typically by hand, and each storage area is closed by returning each door 120 and 134 to a closed position. Once the doors 120 and 134 are closed, the module 60 is rotated about hinge pivots 114 and 116 (see FIG. 2 and FIG. 6) to return the module 60 to its dispensing position. With placement of each of the products in each of the storage areas, the products self-align for proper dispensing within the storage areas when the module 60 is raised to the location of FIG. 2. The holding tray 100 consequently allows for relatively rapid filling of the dispenser 10 with products. There are no vertically oriented shafts or columns having a single loading opening that requires products to be stacked for loading through the single loading opening. Oftentimes, the single loading opening requires that only one or a few products can be loaded at the time. With the completely open storage areas 126, 128, and 138, multiples products can be stored and aligned, if necessary, which saves time. In addition, pre-stacked products, which have a wrapper or strap holding the stack together for loading, are not required. Even when pre-stacked products are used, the wrapper or strap must be removed either by hand or by a mechanism located in a dispenser. Consequently, the loading and dispensing of products as described herein provides a more efficient way to load and to dispense products. Once the products are loaded, the doors 120 and 124 are closed, the module 60 is returned to its location of FIG. 2, and the front door 20 is closed, the dispenser 10 is functional and ready to dispense product.

Figure 5:
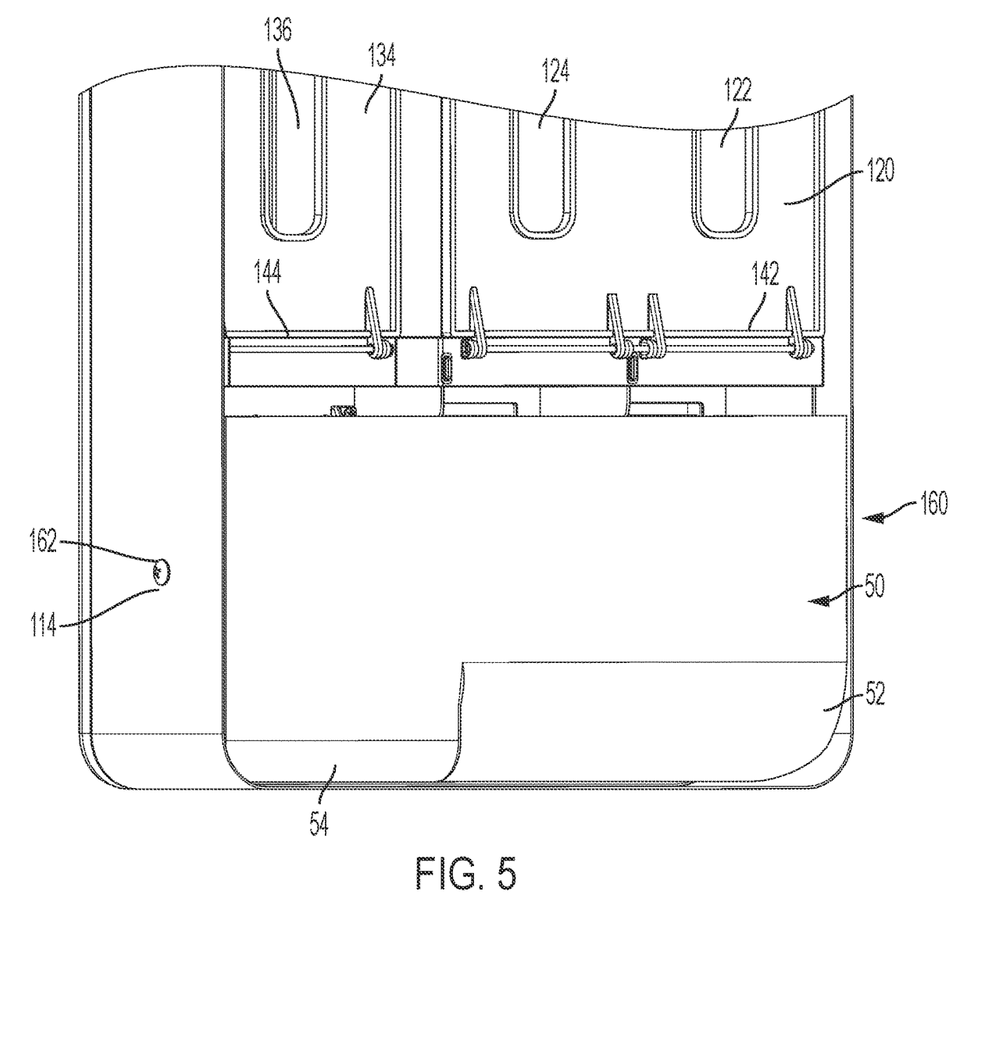
FIG. 5 illustrates an elevational perspective back view of a bottom portion of a dispenser apparatus with a back cover removed.

FIG. 5 illustrates an elevational perspective back view of a bottom portion 160 of the dispenser apparatus 10 with a back cover removed. In this illustration, a backside of the product ramp 50 is illustrated including the first ramp 52 and the second ramp 54. The product ramp 50 is a separate part in this embodiment and is held in place the connectors 162 (one of which is shown) that extend though the side portion at the module hinge pivots 114 and 116. As can be seen, the product ramp 50 defines the ramped portion 52 located below the area enclosed by the door 120 and the ramped portion 54 located below the area enclosed by the door 134.

Removal of the product ramp 50, as illustrated in the perspective back view of FIG. 6, illustrates a first bracket 164 that includes the hinge 142 and which spans a lateral distance across both of the storage areas 126 and 128. The first bracket 164 is attached to the product holding tray 100 on one side and to the divider 152 on the other side. These sides provide a first depth of the tray 100 to accommodate the products 31 and 33. The first bracket 164 also defines dispensing openings with the bottom of the tray 100.

Each of the dispensing openings is located above the first product receiver 89 of FIG. 2 that includes a first dispenser platform 166 and the second product receiver 91 of FIG. 2 having a second dispenser platform 168. The stack of products 31 is supported by platform 166 and the stack or products 33 is supported by platform 168. Each of the platforms is substantially planar and each is configured to support hygiene products that are enclosed in a container, such as a box having flat sides. A stack of boxes is supported by each platform. A second bracket 170, that includes the hinge 144, spans a lateral distance across the storage area 138. The second bracket 170 is attached to the product holding tray 100 on one side and to the divider 152 on the other side. The second bracket 170 includes sides 172, one of which is shown, that determine the depth of the storage area 138. The depth is configured to accept a product of a different size than products located in either of the storage areas 126 and 128. These sides, defined in part by bracket 170, provides a second depth of the tray 100 to accommodate the tampon products 56. The second bracket 170 also defines an opening with the tray 100 which directs the tampon products 56 to a rotatable dispenser 174. A seen in FIG. 4, the depth of the storage area 138 is also determined by the location of the second hinge 144 and the opposing sidewall the tray 100.

Each of the first dispenser platform 166, the second dispenser platform 168, and the rotatable dispenser 174 dispense product toward the product ramp 50 (not illustrated in FIG. 6) and to the product access area 42 across a product deflector 176. Dispensed products are directed away from hitting and possibly damaging product dispensing mechanisms 180, shown in FIG. 7, by the presence of the product deflector 176. The deflector 176 includes a curved surface that directs the dispensed products toward the access area 42.

A product from each column of products is moved by one of a plurality of dispensing mechanisms 180. A seen in FIGS. 7 and 8, there is a first sanitary napkin dispensing system 182, a second sanitary napkin dispensing system 184, and a tampon dispensing system 186. Each of the sanitary napkin dispensing systems 182 and 184 are substantially similar. The discussion of dispensing system 182 therefore applies to the dispensing system 184. In dispensing system, 182 a motor 188A is supported by a bracket 190. Dispensing system 182 include a motor 188B and dispensing system 184 includes a motor 188C. A drive shaft of the motor 188 is integrally affixed to a circular rotating flywheel 192 coupled to a crank arm 194 that rotates in response to rotation of the motor drive shaft. The crank arm 194 is rotatably coupled to the flywheel 192 and to the dispenser platform 166. During operation or after a user activates the sensor 76, a signal is sent to the motherboard 86 to activate motor 188. The power supply 82 powers the motor 188 to rotate the drive shaft (not shown) of motor 188 by three-hundred sixty degrees. The drive shaft and integrally affixed circular rotating flywheel 192 rotate in one direction for approximately 360 degrees. The rotation of circular rotating flywheel 192 causes the crank arm 194 to rotate the dispense platform 166 with respect to first and second pivot supports 196 (see also FIG. 8). As the flywheel 192 rotates, the dispenser platform 166 tilts such that front edge 198 moves downward to drop the hygiene product to the access area 42. The flywheel 192 includes a projection 200 that contacts an arm 202 of a reed switch 204. Since the crank arm 194 is offset from a center location of the flywheel 192, a complete rotation of the flywheel 192 moves the dispense platform 166 from the level support position, as illustrated in FIG. 7, to a tilted position where the product is dropped to the access area 42, and returns to the support position. Further rotation of the flywheel 192 is prevented by the contact of the projection 200 with the arm 202 such that a single product is dispensed with one rotation of the flywheel 192. The switch 204, whose arm is contacted by the projection, transmits a signal to the motherboard 86 which stops the motor 188 until activated again by the sensor 76 being activated.

As seen in FIG. 2, the dispenser platform 166 is connected to the first product door 90 and door flap 92. As the platform 166 rotates to dispense the product, the door flap 92 engages a bottom surface the next product in the stack of products and supports the entire stack as the product is dispensed. The door flap 92 is inclined with respect to a front portion of the door 90 and consequently slides along a surface the next in line product during rotation of the platform 166 as the platform 166 returns to its horizontal position to support the next hygiene product in the stack of products.

In FIG. 8 dispensing system 182 also has a similar configuration of systems 184 and 186 and includes the motor 188, the support 190, the flywheel 192, the crank arm 194 and the switch 204. In this system 186, however, tampons which are generally cylindrical, are supported by a cradle or product dispenser 210. The cradle 210 is pivotally supported by pivot supports 212 as seen in FIG. 8. The pivot supports 212 define the axis of rotation of the cradle 210 which is offset longitudinally from the axis of rotation defined by the pivot supports 196. The cradle 210 extends between the pivot supports and includes three spaced apart disc shaped portions 214 each of which includes a concave surface 216 and a convex surface 218. The concave surface 216 is recessed toward the pivot axis and is configured to support a single tampon product. The convex surface 218 is spaced further from the pivot axis than the concave surface 216 and supports the next in line product and the stack of products while a product located in the concave surfaces 216 of the cradle is being dispensed in response to activation of the motion sensor 80.

The cradle 210 rotates approximately forty-five degrees toward the back wall 25 to cause the product to fall into the access area. The cradle then rotates in the reverse direction toward the front wall by approximately forty-five degrees back to its starting position to return the cradle to its initial position and to retain a successive tampon wherein the time delay prevents a second tampon to be dispensed until the time delay has passed. Upon dispensing of any product, a light bar 211, as seen in FIG. 7, which is coupled to and supported by the deflector 176, is illuminated by controller 220 located at the motherboard 86.

FIG. 9 illustrates further details of an elevational perspective front view the bottom portion of a dispenser apparatus of FIG. 2. A seen in FIG. 9, a controller 220 is supported by the motherboard 86 and is configured to control the operation of the dispenser 10 as further described with regard to FIG. 10. In addition, to the controller 220, the motherboard 86 supports a battery check button 222 and a battery level light 224. To check the battery level, the door 20 is opened to provide access to the door switch 84. By depressing a door switch lever 225 and battery check button 222 at the same time, the battery level light 224 is illuminated. In one embodiment, the battery level light 224 is a two color LED light that provides a first color indicating sufficient battery power and a second color indicating that the batteries need to be changed. For instance, a green light indicates sufficient battery power and a red light indicates that the batteries need to be changed. In other embodiments, the light 224 provides more than three colors to indicate battery levels, for instance, insufficient power, 50% power, 75% power, and 100% power.

Figure 10:
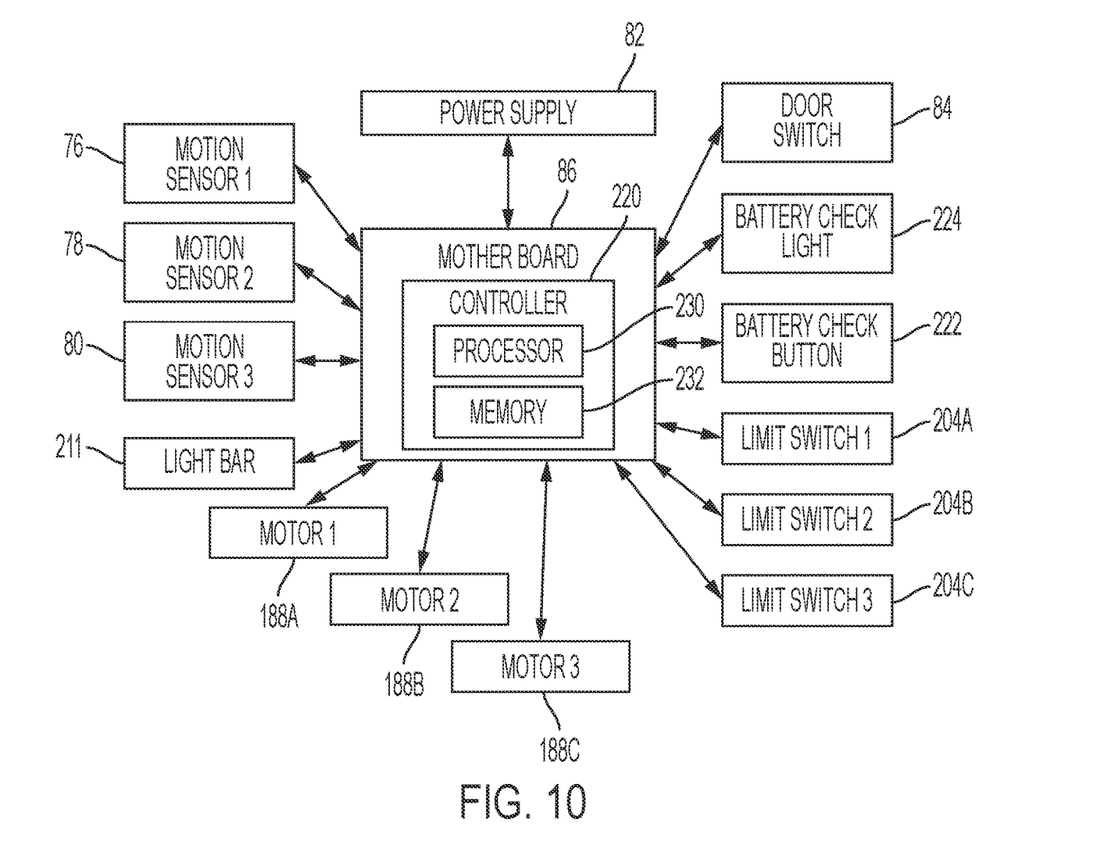
FIG. 10 illustrates a block diagram of a control system of the dispenser apparatus.

As seen in FIG. 10, the motherboard 86 supports the controller 220 which includes a processor 230 and a memory 232. The memory 232 is configured to store program instructions and the processor 230 is configured to execute the stored program instructions in response to transmitted signals received from the user sensor motion sensors 76, 78, and 80. The controller 220 also controls operation of the motors 188A, 188B, and 188C in response to signals received from the motion sensors to dispense products. Once a product is dispensed, the controller 220 illuminates the light bar 211 which illuminates the receiving area 42 for a user to more clearly see the dispensed product. The controller 220 also receives signals generated by limit switches 204A, 204B, and 204C to stop motors from rotating. Additionally, the controller 220 responds to a signal received from the door switch 84 to determine if the door is open or closed. If the door 20 is open, the controller prevents all of the motors 188 from operating. If the door switch 84 indicates that the door is closed, the controller 220 places the dispenser in an operating mode to dispense products or to determine battery levels.

The controller 220 additionally controls operation of the motors in response activation of the sensors 76, 78, and 80 with one or more programmed time delays which delays the dispensing of a second product after a first product has been dispensed. In one embodiment, the processor 230 is programed to include a time delay of 5 seconds. The time delay prevents a second product from being dispensed after a first product is dispensed until the delay of 5 second has elapsed. This time delay applies to products of the same type as well as products of different types. If a second selection of tampon for instance is made before the time delay has elapsed, the dispenser 10 will not dispense the second selected tampon. A selection of a feminine napkin, made before the time delay has elapsed after selection and dispensing of a tampon, will not dispense the selected feminine napkin. Since one or more embodiments of the dispenser dispense products for free, without payment, the delay reduces the likelihood of an individual dispensing too many products which reduces the likelihood of leaving too few products for other individuals.

The controller 220, in different embodiments, includes a computer, computer system, or other programmable devices. In other embodiments, the controller 220 includes one or more processors (e.g. microprocessors or programmable controller chips), with an associated memory, which can be internal to the processor of external to the processor. The memory can include random access memory (RAM) devices comprising the memory storage of the controller 220, as well as any other types of memory, e.g., cache memories, non-volatile or backup memories, programmable memories, or flash memories, and read-only memories. In addition, the memory, in different embodiments, includes a memory storage physically located elsewhere from the processing devices and any cache memory in a processing device, as well as any storage capacity used as a virtual memory, e.g., as stored on a mass storage device or another computer coupled to the controller. The mass storage device can include a cache or other dataspace which can include databases. Memory storage, in other embodiments, is located in the "cloud", where the memory is located at a distant location which provides the stored information wirelessly to the controller 220.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

What is claimed is:

1. A dispensing apparatus for dispensing hygiene products, the apparatus comprising:
   a housing including a back portion, a side portion coupled to the back portion, and a housing door movably coupled to the side portion;
   a module located within the housing and rotatably coupled to the housing at a module pivot, the module including a first side wall, a second side wall, and a front wall defining a tray and further including at least one tray door assembly operatively coupled to the tray, the tray door assembly defining an interior space with the first side wall, the second side wall, and the front wall of the tray, wherein the interior space stores hygiene products to be dispensed, and wherein the module rotates at the module pivot between: i) a lowered position to provide access to the interior space for placement of hygiene products in the interior space; and ii) a raised position to dispense hygiene products from the interior space.

2. The dispensing apparatus of claim 1 wherein the tray door assembly includes a first tray door rotatably coupled to the tray to define a first portion of the interior space, the first portion having a first depth, wherein the first depth is adapted to store a first hygiene product having a first size.

3. The dispensing apparatus of claim 2 wherein the tray door assembly includes a second tray door rotatably coupled to the tray to define a second portion of the interior space, the second portion having a second depth, wherein the second depth is adapted to store a second hygiene product having a second size different than the first size.

4. The dispensing apparatus of claim 3 wherein the first hygiene product is a tampon and the second hygiene product is a sanitary napkin.

5. The dispensing apparatus of claim 3 wherein the module rotates in a first direction away from the housing to enable the first tray door and the second tray door to move in a second direction different than the first direction to expose the interior space for placement of the first and second hygiene products in the first portion and the second portion of the interior space.

6. The dispensing apparatus of claim 5 wherein the module includes a divider disposed in the interior space of the tray, the divider extending along a length of the tray to define the first portion and the second portion of the interior space.

7. A dispensing apparatus for dispensing hygiene products, the apparatus comprising:
a housing including a back portion, a side portion coupled to the back portion, and a housing door movably coupled to the side portion;
a module rotatably coupled to the housing, the module including a tray and at least one tray door assembly operatively coupled to the tray, the tray door assembly defining an interior space with the tray, wherein the interior space stores hygiene products to be dispensed;
wherein the tray door assembly includes a first tray door rotatably coupled to the tray to define a first portion of the interior space, the first portion having a first depth, wherein the first depth is adapted to store a first hygiene product having a first size;
wherein the tray door assembly includes a second tray door rotatably coupled to the tray to define a second portion of the interior space, the second portion having a second depth, wherein the second depth is adapted to store a second hygiene product having a second size different than the first size;
wherein the module rotates in a first direction away from the housing to enable the first tray door and the second tray door to move in a second direction different than the first direction to expose the interior space for placement of the first and second hygiene products in the first portion and the second portion of the interior space;
wherein the module includes a divider disposed in the interior space of the tray, the divider extending along a length of the tray to define the first portion and the second portion of the interior space; and
wherein the module includes a positionable divider having a first position and a second position, wherein the divider in the first position defines the first portion and second portion to have the same width, and the divider in the second position defines the first portion and the second portion to have different widths.

8. The dispensing apparatus of claim 7 wherein the module includes a bottom portion located adjacent to the tray and a dispensing device located at the bottom portion, wherein the dispensing device dispenses the first hygiene product and the second hygiene product.

9. The dispensing apparatus of claim 8 wherein the dispensing device includes a first dispenser to dispense the first hygiene product and a second dispenser to dispense the second hygiene product.

10. The dispensing apparatus of claim 9 wherein the first dispenser rotates about a first axis and includes a convex surface to engage the first hygiene product, and the second dispenser rotates about a second axis and includes a flat surface configured to engage the second hygiene product.

11. The dispensing apparatus of claim 10 wherein the first dispenser includes a concave surface disposed adjacent to a convex surface, wherein the first dispenser in a first position captures a first one of the first hygiene product with the concave surface for dispensing and in a second position supports a second one of the first hygiene product while the first one of the first hygiene product is being dispensed.

12. The dispensing apparatus of claim 11 wherein the second dispenser includes a flap disposed adjacent to a flat surface, wherein the second dispenser in a first position supports a first one of the second hygiene product with the flat surface and the second dispenser in a second position supports a second one of the second hygiene product prior to being dispensed.

13. The dispensing apparatus of claim 12 wherein the dispensing device includes a first motor connected to the first dispenser to move the first dispenser to a first position to receive one of the first hygiene product to a second position to dispense the received first hygiene product.

14. The dispensing apparatus of claim 13 wherein the dispensing device includes a second motor connected to the second dispenser to move the second dispenser from a first position to receive one of the second hygiene product to a second position to dispense the received second hygiene product.

15. The dispensing apparatus of claim 14 further comprising a deflector disposed adjacent to the first dispenser and to the second dispenser, wherein the deflector deflects the first hygiene product and the second hygiene product away from the first motor and the second motor.

16. A dispensing apparatus for dispensing hygiene products, the apparatus comprising:
a housing including a back portion, a side portion coupled to the back portion, and a housing door movably coupled to the side portion; and
a module located within the housing and rotatably coupled to the housing at a module pivot, the module including a first side wall, a second side wall, and a front wall defining a tray having an interior space to temporarily store hygiene products, a divider located in the interior space of the tray to divide the interior space into a first portion and a second portion, a first tray door rotatably coupled to the tray to limit access to the first portion when the first tray door is closed, and a second tray door rotatably coupled to the tray to limit access to the second portion when the second tray door is closed;
wherein the module rotates at the module pivot between: i) a lowered position to provide access to the interior space for placement of hygiene products in the interior space; and ii) a raised position; and
wherein the module includes a bottom portion located adjacent to the tray and a dispensing device located at the bottom portion, wherein the module in the raised position positions the hygiene products for the dispensing device to dispense the the hygiene products.

17. The dispensing apparatus of claim 16 wherein the dispensing device includes a first dispenser to dispense the first hygiene product and a second dispenser to dispense the second hygiene product.

18. The dispensing apparatus of claim 17 wherein the first portion of the interior space has a first depth adapted to store a first hygiene product having a first size and the second portion of the interior space has a second depth adapted to store a second hygiene product having a second size.

19. The dispensing apparatus of claim 18 wherein the module rotates in a module opening direction away from the housing to the lowered position to enable the first tray door and the second tray door to move in directions different than the module opening direction to expose the interior space for placement of the first and second hygiene products in the first portion and the second portion of the interior space.

20. A method of dispensing hygiene products comprising:
enabling the rotation of a hygiene product module away from a housing when a housing door is in an open position to expose a module door of the hygiene product module;
releasing the module door from the hygiene product module to enable rotation of the module door with respect to the hygiene product module and to expose a space in the module;
supporting hygiene products in the space;
temporarily storing the supported hygiene products in the space upon latching of the module door to the module;
enabling the rotation of the hygiene product module toward the housing to restrict access to the space in the hygiene product module;
dispensing the stored hygiene products from the space once the housing door is closed and access to the space in the module is restricted;
deflecting the dispensed stored hygiene products away from module electronics towards a dispensing shelf; and
illuminating a light upon the dispensing of one of the stored hygiene products.

* * * * *